(12) United States Patent
Garson et al.

(10) Patent No.: US 12,721,949 B2
(45) Date of Patent: Sep. 1, 2026

(54) CONTAINER HOLDER FOR ADAPTING SMALLER DIAMETER CONTAINER

(71) Applicant: Owen Mumford Limited, Woodstock (GB)

(72) Inventors: Daniel Garson, Woodstock (GB); Andreas Artelsmair, Woodstock (GB); Brady King, Woodstock (GB)

(73) Assignee: Owen Mumford Limited, Woodstock (GB)

( * ) Notice: Subject to any disclaimer, the term of this patent is extended or adjusted under 35 U.S.C. 154(b) by 976 days.

(21) Appl. No.: 17/278,449

(22) PCT Filed: Sep. 20, 2019

(86) PCT No.: PCT/EP2019/075402
§ 371 (c)(1),
(2) Date: Mar. 22, 2021

(87) PCT Pub. No.: WO2020/064572
PCT Pub. Date: Apr. 2, 2020

(65) Prior Publication Data

US 2021/0353860 A1 Nov. 18, 2021

(30) Foreign Application Priority Data

Sep. 28, 2018 (GB) ..................................... 1815869

(51) Int. Cl.
*A61M 5/20* (2006.01)
*A61M 5/19* (2006.01)
(Continued)

(52) U.S. Cl.
CPC ................ *A61M 5/19* (2013.01); *A61M 5/20* (2013.01); *A61M 5/3134* (2013.01);
(Continued)

(58) Field of Classification Search
CPC ............ A61M 5/24; A61M 2005/2403; A61M 2005/2477; A61M 2005/2433; A61M 2005/2407; A61M 2005/2485
See application file for complete search history.

(56) References Cited

U.S. PATENT DOCUMENTS 2,672,868 A * 3/1954 Hickey .................. A61M 5/24 604/234
3,742,948 A 7/1973 Post et al.
(Continued)

FOREIGN PATENT DOCUMENTS

TW 201811383 A 4/2018
WO 2006058435 A2 6/2006
WO 2015104694 A1 7/2015

OTHER PUBLICATIONS

International Search Report and Written Opinion of the International Searching Authority from corresponding PCT Application No. PCT/EP2019/075402, dated Jan. 22, 2020 (13 pages).
(Continued)

*Primary Examiner* — Laura A Bouchelle
*Assistant Examiner* — Sarah Dympna Grasmeder
(74) *Attorney, Agent, or Firm* — Greenberg Traurig, LLP

(57) ABSTRACT

A housing suitable for use with one of a plurality of containers containing a medical substance, wherein the plurality of containers have different outer diameters, the housing comprising: one or more internal projections at a distal side of the housing for blocking distal movement of a first container when the first container is received within the housing, wherein the first container has a first external diameter; one or more inwardly projecting ridges provided proximally from said one or more internal projections, wherein the ridges are suitable for blocking distal movement of a container holder which holds a second container when the container holder is received within the housing, wherein
(Continued)

the second container has a second external diameter which is smaller than the first external diameter.

12 Claims, 6 Drawing Sheets

(51) Int. Cl.
*A61M 5/31* (2006.01)
*A61M 5/24* (2006.01)

(52) U.S. Cl.
CPC ............... *A61M 2005/2403* (2013.01); *A61M 2005/2433* (2013.01); *A61M 2005/2477* (2013.01); *A61M 2005/3132* (2013.01)

(56) References Cited

U.S. PATENT DOCUMENTS 9,173,995 B1 * 11/2015 Tucker ................ A61M 5/1408
9,901,680 B2 2/2018 Roervig
2014/0048432 A1 2/2014 Kakiuchi et al.
2014/0330203 A1 * 11/2014 McLoughlin ........... A61M 5/20 604/131
2014/0330207 A1 11/2014 McLoughlin et al.
2015/0112259 A1 * 4/2015 Holmqvist .......... A61M 5/5086 604/111
2015/0273158 A1 10/2015 Cowe
2016/0074584 A1 * 3/2016 Carmel ............... A61M 5/2033 604/218
2016/0095981 A1 * 4/2016 Soerensen ......... A61M 5/31563 604/211
2016/0101235 A1 * 4/2016 Holmqvist .............. A61M 5/20 604/197
2018/0140781 A1 5/2018 Kemp et al.

OTHER PUBLICATIONS

Search and Examination Report, related UK Application No. GB1815869.1, mailed Mar. 26, 2019, 6 pages.
Examination Report, related UK Application No. GB1815869.1, mailed Feb. 5, 2021, 2 pages.
Office Action for corresponding Chinese Patent Application No. 201980063769.9, dated Apr. 24, 2022 (15 pages).
International Preliminary Report on Patentability from corresponding PCT Application No. PCT/EP2019/075402 dated Apr. 8, 2021 (9 pages).

* cited by examiner

CONTAINER HOLDER FOR ADAPTING SMALLER DIAMETER CONTAINER

CROSS-REFERENCE TO RELATED APPLICATIONS

The present application represents the United States National Stage of International Application No. PCT/EP2019/075402, filed Sep. 20, 2019, which relates to and claims priority to British Patent Application Serial No. GB 1815869.1, filed Sep. 28, 2018, both of which are incorporated herein by reference in their entirety.

The present invention relates to substance delivery devices and in particular to injection devices for delivering a medical substance to a user or patient via a syringe Injection devices are used for the convenient administration of medicaments to patients. For example, injection devices, which may be auto-injectors, may be used for providing a single metered dose of a medicament. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may be provided in the form of an auto-injector device, in which delivery of the medicament is automated and the device may also be arranged to automate the insertion of a needle into the skin prior to the delivery of the medicament. However, it is noted that the term auto-injector may encompass injection devices that automatically insert the needle and devices which require the user to manually insert the needle. As used in the present specification, the term 'distal' is intended to designate a location of direction towards the injection site of the user's skin, and the term 'proximal' is intended to designate a location or direction away from the user's skin.

Injection devices generally comprise a firing mechanism that is arranged to deliver a fluid from the syringe automatically under the force of a drive system, such as a drive spring. Optionally, injection devices may also comprise an insertion mechanism to displace the syringe within a housing of the injection device to cause needle penetration. The delivery arrangement generally acts via a plunger which includes a plunger and may also include or engage a piston (also referred to as a "bung") which is slidably provided within the syringe.

It is desirable to use a generic device which is suitable for use with a range of different containers, in particular containers with a range of different external diameters.

According to a first aspect of the invention, there is provided a housing suitable for use with one of a plurality of containers containing a medical substance, wherein the plurality of containers have different outer diameters, the housing comprising: one or more internal projections at a distal side of the housing for blocking distal movement of a first container when the first container is received within the housing, wherein the first container has a first external diameter; one or more inwardly projecting ridges provided proximally from said one or more internal projections, wherein the ridges are suitable for blocking distal movement of a container holder which holds a second container when the container holder is received within the housing, wherein the second container has a second external diameter which is smaller than the first external diameter.

One or more windows may be provided proximally from the one or more internal projections and offset along the circumferential direction from the one or more internal projections. Guide rails may also be provided for guiding a guiding portion of the container holder.

According to a second aspect of the invention, there is provided a container holder for use with a container containing a medical substance and for use with a substance delivery device, the container holder comprising: a cylindrical portion; a plurality of flexible arms extending from the cylindrical portion in a distal direction, wherein the plurality of flexible arms are disconnected from each other at their distal ends.

A shoulder may be provided around at least part of the outside of the cylindrical portion and extending in radial direction of the cylindrical portion. At least one of the plurality of flexible arms may comprise a radially inwards projection. The cylindrical portion and the plurality of flexible arms may define an inner bore which tapers radially inwards towards the radially inwards projection. A guiding portion may be provided which projects radially outwards from the cylindrical portion, and the guiding portion may at least be partially tapered in distal direction.

According to a third aspect of the invention there is provided an assembly comprising the housing according to the first aspect and a container holder according to the second aspect, wherein when the container holder is fit within the housing, the one or more internal projections of the housing project between the plurality of flexible arms of the container holder.

The housing may at least partially enclose the flexible arms to prevent the flexible arms from flexing radially outwards. The housing may comprise a plurality of windows whereby the number of windows in the housing is equal to the number of flexible arms of the container holder and the flexible arms block the widows.

The guiding portion of the container holder may be received within the guide rails of the housing.

Some embodiments of the invention will now be described by way of example only and with reference to the accompanying drawings, in which.

Figure 1:
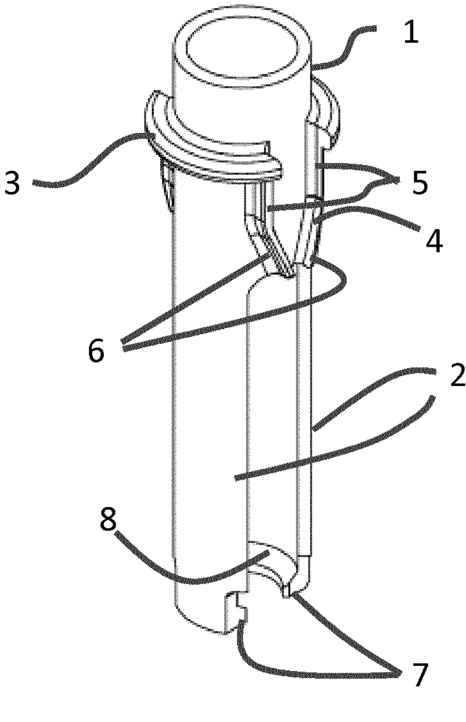
FIG. 1 shows a perspective view of container holder according to a first embodiment of the present invention.
Figures 2, 3, 4:
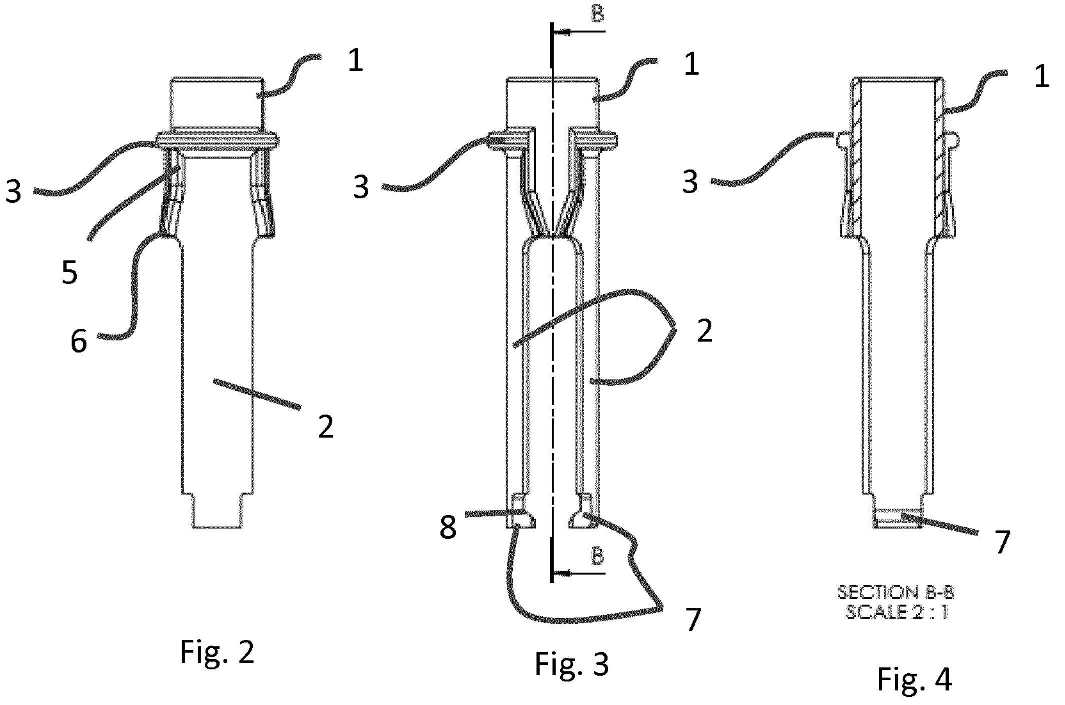
FIG. 2 shows a side view of the container holder shown in FIG. 1.
FIG. 3 shows a side view of the container holder shown in FIG. 1, whereby the view is perpendicular to the view of FIG. 2.
FIG. 4 is a longitudinal section through the container holder of FIGS. 1 to 3, along the section plane B-B shown in FIG. 3.

Injection devices may be designed and manufactured to accommodate different syringes. This provides a device that may be adapted to carry and operate syringes with different features and/or characteristics, such as different fill volumes. It is desirable to improve the safety and operability of such devices.

The inventors have appreciated that a container holder can be used for holding a container within an internal space of a housing. The outer diameter of the container is smaller than the internal space of the housing. The internal space of the housing would be too large for the container without the container holder and the container would be able to move around without a snug fit and become misaligned or damaged due to movement against the housing. The same internal space of the housing can also receive a container with a larger outer diameter than the diameter of the earlier mentioned container without requiring the container holder. A generic housing is provided which is suitable for use with containers with different outer diameters.

The container holder can be manufactured and/or provided to users separately from the housing and separately from the container. The container holder also does not need to be device-specific because the container holder can have a shape which increases the outer diameter of a smaller container to match the outer diameter of a larger container, and any device suitable for use with the larger container would therefore also be suitable for use with the combined smaller container and container holder. Containers such as syringes can be used in many different substance delivery devices provided by different manufacturers and therefore the container holder described herein can also be used in many different substance delivery devices.

A specific example of a container is a syringe, but other containers can also be used. A syringe typically includes an injection needle, but needleless devices are also common devices for medical substance delivery. A needleless device ejects the medical substance at a high velocity such that the medicament enters the user's body through the skin without the use of a needle. Alternatively, a cartridge with a separate screw-on needle can be provided.

Both the smaller diameter container and the larger diameter container generally have a cylindrical shape and the container holder has an at least partially tubular shape to adapt the diameter of the smaller container to match the diameter of the larger container. The container holder has at least one radially inwards projection at the distal end to prevent the container from slipping out of the container holder when pressure is applied to the proximal end of the container, for example when a plunger acts on a bung during firing of a syringe.

The container holder can be fit around the smaller container before the smaller container is placed in the substance delivery device. The container often has a cap, or other protective cover to keep the distal part sterile. In particular, a syringe typically has a rigid needle shield (RNS) which covers the needle to keep the needle sterile before use and also to protect a user from accidental injury from the needle. The cover needs to be removed before use of the substance delivery device and the cover is therefore not blocked by said radially inwards projection which prevents the container from slipping out of the container holder in distal direction. The container holder has a flexible arm to which the radially inwards projection is attached and the flexible arm bends outwards when a container with a protective cover is inserted such that the protective cover can exit the container holder. The flexible arm moves back to its original position after the cover has been moved outside the container holder. A plurality of flexible arms with radially inwards projections are provided which are preferably distributed symmetrically around the circumference of the container holder to distribute forces symmetrically. The flexible arms are not connected to one another at the distal end and can therefore flex independently.

In a further embodiment, the container holder has a shoulder which extends in a radially outwards direction from the main cylindrical part of the container holder. The shoulder can be used to hang the container holder off a corresponding ridge within a housing of a substance delivery device or for improved grip when holding the container holder by hand. The container holder further has a guiding portion extending radially outwards which tapers in distal direction for guiding the container holder into a receiving slot within a housing.

FIGS. 1 to 4 illustrates a specific embodiment of the container holder. In the specific embodiments, the container holder is also referred to as a syringe holder, and the container is also referred to as a syringe. The container holder generally has a tubular shape, with a first cylindrical portion 1 having a cylindrical outer portion and defining a bore. The outer diameter of the cylindrical portion 1 matches the outer diameter of a large volume syringe, while the diameter of the bore matches the outer diameter of a small volume syringe. The container holder can therefore be used as an adapter to make the small volume syringe fit within a housing designed for the large volume syringe. The first cylindrical portion 1 extends into a second portion with two flexible arms 2. Flexible arms 2 are sections of a tubular with the same inner diameter and outer diameter as first cylindrical portion 1 such that flexible arms can also function as an adapter. The flexible arms can flex inwards and outwards in radial direction. The two flexible arms are not connected to each other at their distal end and can therefore move independently from each other. Two flexible arms are shown in this embodiment, but a larger number of flexible arms, such as 3 or 4, can also be provided while providing the same technical functions as two arms.

A shoulder 3 is provided which extends radially outwards from the first cylindrical portion 1 and which further extends in circumferential direction. The shoulder is provided partway down in distal direction from the proximal end of the first cylindrical portion in the illustrated embodiment, but can alternatively be provided at the proximal end of the first cylindrical portion. The shoulder can be used to hang the container holder off an abutment surface within a housing or for a better grip when holding the container holder. The shoulder is interrupted in circumferential direction by a guiding portion 4 which extends radially outwards in distal direction and which is tapered in distal direction. In the illustrated embodiment two guiding portions are provided on either side of the container holder and above the opening between flexible arms 2. The tapered portion guides the container holder into a corresponding slot within the housing to fix the orientation of the container holder in radial direction, thereby preventing rotation. Each guiding portion 4 includes two parallel projections 5 extending into two projections 6 which approach each other in distal direction and form the tapered portion.

The flexible arms 2 terminate into inwards projections 7 which project radially inwards into the bore and which carry out the function of retaining a container within the container holder. The projections have an angled inside surface 8 at their proximal side. When a force is applied onto the angled surface in distal direction by a cap, for example, the angled surface will cause the arm to flex outwards, which will enable the cap to move past the arms.

FIGS. 5 to 9 illustrate a housing 51 of an injection device, wherein the housing can accommodate a range of containers with different external diameters. Small containers can be housed in combination with a container holder, while a large diameter container can be fit into the housing without a container holder.

Housing 51 includes two internal projections 52 which extend into a bore defined by the housing. Although two internal projections 52 are illustrated, one projection or any number of projections larger than two can also be used. A syringe rests in use against the internal projections and the internal projections therefore prevent a syringe from falling out of the housing in distal direction. A typical syringe has a flange at its proximal end, but the flange is preferably not used for holding the syringe because the flange is prone to breaking due to the forces during substance delivery.

When using a combined syringe holder and a small diameter syringe, the syringe holder will not rest on internal projections 52, but instead rest on an inwardly projecting ridge 53 with shoulder 3. When using a large diameter syringe, the syringe rests on internal projections 52, but a small diameter syringe instead rests on inwards projections 7 of the container holder. The distance between internal projections 52 is larger than some small diameter syringes and the small diameter syringe would therefore slip past the internal projections 52 without the syringe holder keeping the small diameter syringe in place with inwards projections 7. Neither the small diameter syringe nor the large diameter syringe will rest on a flange of the syringe.

Figures 5, 6, 7, 8, 9:
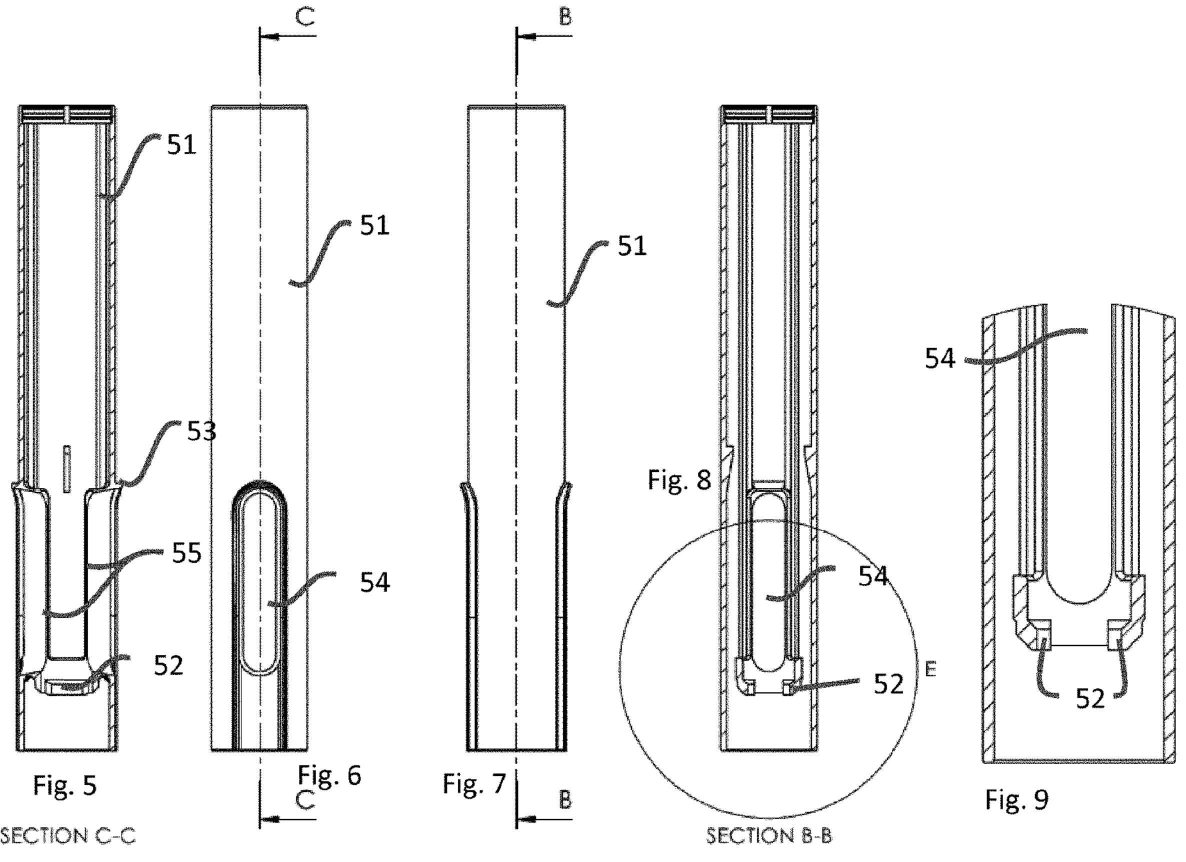
FIG. 5 shows a section of a housing according to a second embodiment of the present invention. The section is along the section place C-C illustrated in FIG. 6.
FIG. 6 shows a side view of a housing according to the second embodiment of the invention.
FIG. 7 shows a side view of the housing according to the second embodiment, whereby the side view is perpendicular to the side view of FIG. 6.
FIG. 8 shows a longitudinal section along section plane B-B shown in FIG. 7.
FIG. 9 is an enlarged Figure of area E encircled in FIG. 8.

In the specific embodiment illustrated in FIG. 5, there are two internal projections 52 and two windows 54. In circumferential direction, the two internal projections are provided in between the two windows 54 and the internal projections are offset from the windows by 90 degrees along the circumferential direction. When the syringe holder is placed inside the housing, the two flexible arms 2 are in front of the windows. The flexible arms are made of a transparent material such that the syringe is visible and the substance within the syringe can be inspected. The flexible arms protect the syringe from direct exposure to users or objects in the environment through the windows of the housing. The internal projections 52 and inwards projections 7 dovetail together, whereby the internal projections fit between the inwards projections and the container holder is prevented from rotating.

The two flexible arms 2 are wider and longer than the windows and therefore cannot flex outwards after being placed within the housing. The housing restricts the movement of the flexible arms outwards. Therefore, after the syringe and syringe holder have been placed into the housing, the syringe will not be able to move past the inwards projections 7. The RNS or other cover can be removed by pulling it in distal direction because it is provided on the distal side of the inwards projections 7.

When a syringe is placed in the housing, the rotational orientation of the syringe is not relevant because the syringe is rotationally symmetric. When the syringe holder is placed in the housing, however, the features of the syringe holder and the housing cooperate as described above and the orientation needs to be correct. The correct orientation during insertion is helped by guiding features on the container holder and the housing. The container holder includes the guiding portion 4 with two parallel projections 5 extending into two tapered projections 6. The guiding portion 4 is received by with guiding rails 55 within the housing. The tapered projections 6 help to align the parallel projections 5 with the guiding rails 55.

By way of illustration, an auto injector is described with reference to FIGS. 10 to 12. The auto injector incorporates a housing 118 and a syringe holder 118' as described above, but the invention is not limited to use with the auto injector illustrated by way of background in FIGS. 10 to 13.

Figure 11:
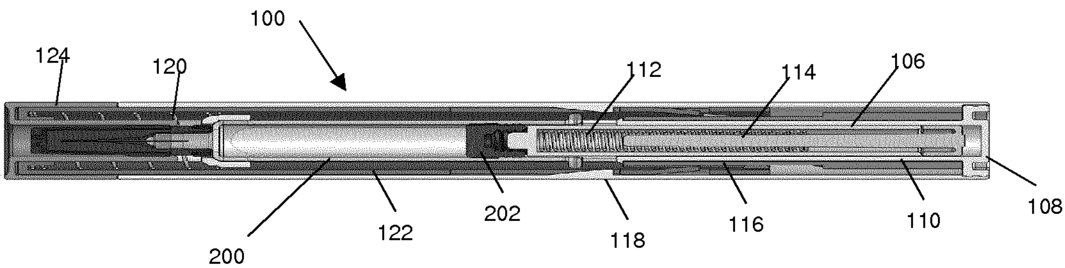
FIG. 11 illustrates an auto injector.
Figure 12:
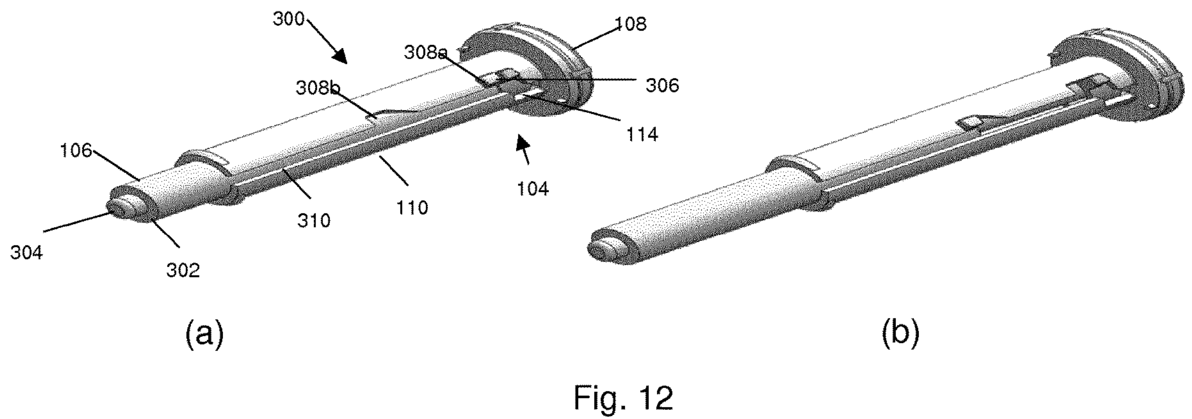
FIG. 12 illustrates an auto injector.

FIG. 11 shows an exploded view of an auto-injector 100. The auto-injector 100 comprises a firing assembly 102. The firing assembly comprises a rear cap 104 and a plunger 106. The rear cap 104 comprises a head 108 and an elongate member 110.

The rear cap 104 and the plunger 106 are connected to each other such that before firing, relative axial movement between them is resisted or prevented. The connection between the rear cap 104 and the plunger 106 is releasable such that after activation of the auto-injector 100, relative axial movement between them is permitted. The nature of the releasable connection is discussed in more detail below.

The firing assembly 102 also comprises a biasing member 112 for driving the plunger 106 axially forwards and into a barrel of a syringe (shown in FIG. 11) retained within the auto-injector 100. In one example the biasing member 112 is a drive spring (e.g. a compression spring) and will be referred to as such throughout, although this should not be construed as limiting and the skilled person will appreciate that other means may be used to drive the plunger forwards.

Figure 10:
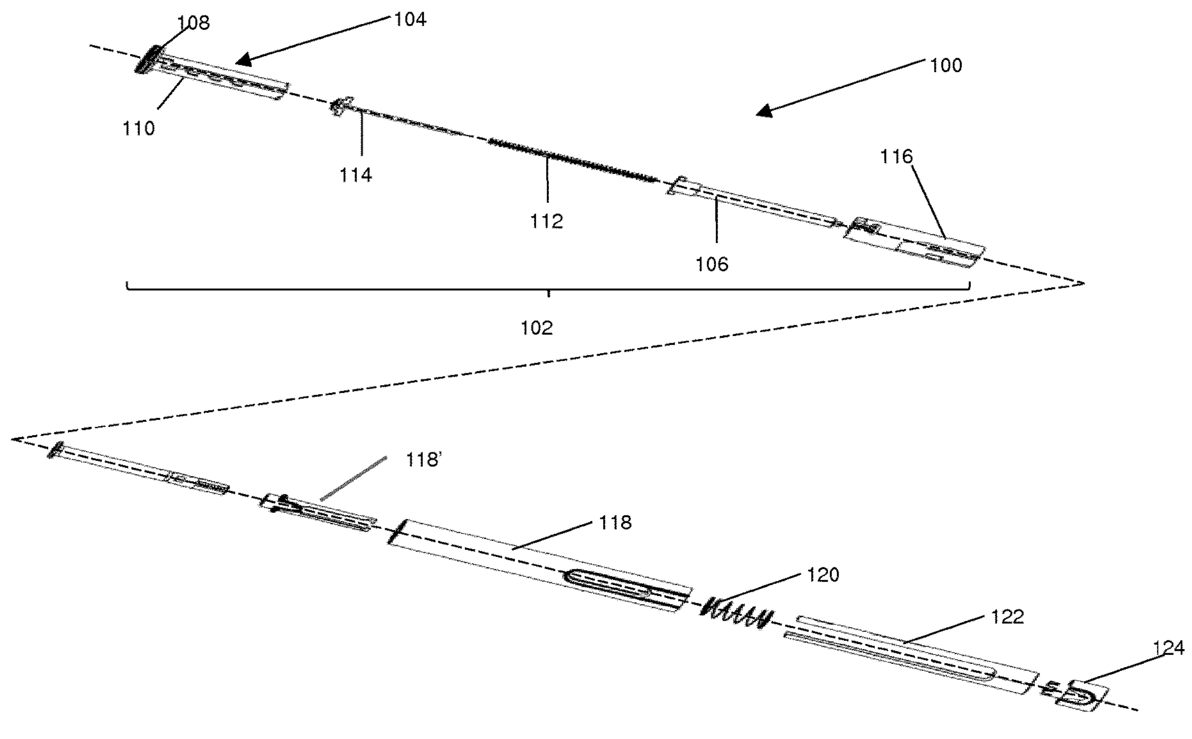
FIG. 10 illustrates an auto injector.

In the example of FIG. 10, the plunger 106 is telescopically received within the elongate member 110 of the rear cap 104. The drive spring 112 is positioned between the rear cap 104 and the plunger 106 such that they are biased in opposite axial directions relative to each other. This is best shown in FIG. 11, which is a section through an auto-injector 100 in an assembled state before activation and with a syringe 200 retained therein. The plunger 106 is received within the elongate member 110. The plunger (106) is a hollow tube with an open end at the rear and the drive spring 112 is received within the plunger 106. A first end of the drive spring 112 abuts a forward end of the plunger 106 and a second end of the drive spring 112 is fixed with respect to the rear cap at least during delivery of a medicament from the syringe. In some exemplary arrangements, the second end of the drive spring 112 may be coupled to (i.e. directly or indirectly abuts or is connected to) a reaction surface on the rear cap 104 or a further member directly or indirectly axially coupled to the rear cap 104. In the example of FIG. 11, the drive spring 112 is coupled to an end of dose indicator 114, which in turn is coupled to the rear cap 104. Expansion of the drive spring 112 drives the plunger 106 forwards into the barrel of the syringe 200 because, in the example of FIGS. 10 and 11, the position of the rear cap 104 is fixed.

In FIG. 11, a forward end of the plunger (106) is shown abutting a bung 202. This will not always be the case, as discussed above.

The auto-injector 100 also comprises a clutch 116, which is positioned around the elongate member 110. Before activation of the auto-injector 100, the clutch 116 is rotationally coupled to the plunger 106. Rotation of the clutch 116 therefore causes rotation of the plunger 106. As explained below, on activation of the auto-injector 100, the clutch 116 rotates, thereby rotating the plunger 106 relative to the rear cap 104 to release the connection therebetween. Operation of the clutch 116 is explained in more detail below.

The auto-injector 100 also comprises a main body 118, which houses the firing mechanism 102, the syringe 200 and other features necessary for operation of the auto-injector 100. The main body 118 may comprise a plurality of separate parts. The main body 118 comprises a syringe locator, which in exemplary arrangements comprises one or more features for receiving and optionally retaining a syringe in position within the main body 118.

The auto-injector also comprises a lockout spring 120 and lockout shroud 122, wherein the lockout spring 120 is configured on release thereof to displace the lockout shroud 122 axially forwards to cover a needle of the syringe. A cap 124 also forms part of the auto-injector and covers a needle or forward end of the auto-injector prior to use.

FIGS. 12*a* and 12*b* show perspective views of an assembly 300 for a firing mechanism. The assembly 300 comprises the rear cap 104 and the plunger 106. The plunger 106 is telescopically received within the elongate member 110. The assembly 300 also comprises a plunger driver to drive the plunger 106 axially forwards, which in the exemplary arrangements disclosed herein comprises a compression spring although the skilled person will understand that other arrangement are possible. The exemplary assembly 300 may also comprises an end of dose indicator 114.

The exemplary plunger 106 comprises a cylindrical tube that is open at a rear end and closed at a forward end. The forward end of the plunger 106 comprises a shoulder 302 and a projection 304 configured to engage a bung 202 in a syringe barrel. The plunger 106 also comprises a lug 306 configured to engage with any of a plurality of recesses 308*a*, 308*b* in the elongate member 110. In the exemplary arrangements of FIGS. 12*a* and 12*b* the lug 306 extends radially from on outer surface of the plunger 106.

The elongate member 110 comprises an axial channel 310. The plurality of recesses 308*a*, 308*b* are formed in a sidewall of the channel 310. That is, the plurality of recesses 308*a*, 308*b* extend circumferentially (or transverse to the axial channel) around the outer wall of the elongate member 110. It is noted that while only two recesses 308*a*, 308*b* are shown in FIGS. 12*a* and 12*b*, more recesses may be provided in the elongate member 110. The recess 308*b* comprises an angled rear surface and a front surface that is perpendicular to an axial direction (or longitudinal axis) of the auto-injector 100. The recesses 308*a*, 308*b* are configured to receive the lug 306 of the plunger 106. FIG. 12*a* shows the lug 306 received in a rearward recess 308*a* and FIG. 12*b* shows the lug 306 received in a forward recess 308*b*.

The channel 310 and the recesses 308*a*, 308*b* are configured such that rotation of the plunger rd 106 relative to the elongate member 110 in a first direction moves the lug 306 into the recesses 308*a*, 308*b* and rotation in a second, opposite direction moves the lug 306 out of the recesses 308*a*, 308*b*.

The plunger 106 and the rear cap 104, in particular the elongate member 110, define an axial length of the assembly 300. The axial length of the assembly 300 determines a start position of the forward end of the plunger 106 before release of the connection of the plunger 106 the elongate member 110. This can be seen in FIGS. 12*a* and 12*b*, which show the plunger 106 releasably connected to the elongate member 110 at different points, thereby controlling the overall axial length of the assembly 300.

Operation of the auto-injector 100 is described below using the reference numerals of the exemplary arrangement shown in FIGS. 10 and 11. Other arrangements of the firing mechanism assembly may be used and the appropriate reference numerals may therefore be substituted into the following description.

In use, a user removes the cap 124 of the auto-injector 100, which in turn removes a rigid needle shield covering the needle. Removal of the cap exposes the lockout shroud 122, which protrudes from a forward end of the body 118.

The user places a forward end of the lockout shroud 122 against an injection site and pushes the auto-injector 100 downwards onto the injection site. This action pushes the lockout shroud 122 rearwards within the auto-injector 100. The lockout shroud interacts with the clutch 116 to rotate it. This may be done by forcing a surface (or pip) of the lockout shroud 122 against an angled surface on the clutch 116, which translates the rearward motion of the lockout shroud 122 into rotational motion of the clutch 116.

In some arrangements, an insertion spring may be activated by the action of pushing the auto-injector 100 onto the injection site and the insertion spring may drive the syringe forwards within the device to insert the needle into the injection site. In other arrangements, the force applied by the drive spring 112 acting against the bung may be used to insert the needle. In yet further arrangements, the syringe may be fixed in relation to the injection device 100 and the force applied by the user when pushing the auto-injector 100 onto the injection site may insert the needle into the injection site.

As the clutch 116 is rotationally coupled to the plunger 106, rotation of the clutch 116 causes rotation of the plunger 106. In some arrangements, the clutch 116 may have an internal track located on an internal wall thereof and that receives a lug of the plunger 106. The lug may be the same as the lug 306 described with reference to FIGS. 12*a* and 12*b*. Rotation of the plunger 106 with respect to the rear cap 104 releases the connection between the rear cap 104 and the plunger 106, allowing the plunger 106 to be driven forwards under force of the drive spring 112. In the examples of FIG. 12, this is provided by rotating the lug 306 of the plunger 106 out of whichever recess 308*a*, 308*b* the lug 306 was positioned in and into the axial channel 310. The lug 306 is thereby allowed to travel forwards within the channel 310.

The drive spring 112 then acts against the plunger 106 and the rear cap 104. Because the rear cap 104 is fixed within the auto-injector 100, the force delivered by the drive spring 112 acts to drive the plunger 106 into the barrel of the syringe.

After delivery of the contents of the syringe 200, the lockout shroud is deployed under force of the lockout spring 120 in any of a number of ways that will be apparent to the skilled person.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. An assembly for delivery of a medical substance comprising:

a housing suitable for use with one of a plurality of containers containing a medical substance, wherein the plurality of containers have different outer diameters; and a container holder for receipt within the housing and comprising a shoulder at a proximal end of the container holder, wherein the housing comprises one or more internal projections at a distal end of the housing for blocking distal movement of a first container when the first container is received within the housing, wherein the first container has a first external diameter, and wherein the housing further defines one or more inwardly projecting ridges provided proximally from said one or more internal projections, wherein the one or more ridges are configured to abut the shoulder to block distal movement of the container holder, which holds a second container, when the container holder is received within the housing, wherein the second container has a second external diameter which is smaller than the first external diameter, and wherein the second container, when received within the container holder, extends distally from the shoulder.

2. The assembly of claim 1, wherein the housing further comprises one or more windows provided proximally from the one or more internal projections and offset along the circumferential direction from the one or more internal projections.

3. The assembly of claim 1, wherein the housing further comprises guide rails for guiding a guiding portion of the container holder.

4. The assembly of claim 1, wherein the container holder comprises:

a cylindrical portion; and a plurality of flexible arms extending from the cylindrical portion in a distal direction, wherein the plurality of flexible arms are disconnected from each other at their distal ends.

5. The assembly according to claim 4, wherein the shoulder is provided around at least part of the outside of the cylindrical portion and extending in a radial direction of the cylindrical portion.

6. The assembly according to claim 4, wherein at least one of the plurality of flexible arms comprises a radially inwards projection.

7. The assembly according to claim 6, wherein the cylindrical portion and the plurality of flexible arms define an inner bore which tapers radially inwards towards the radially inwards projection.

8. The assembly according to claim 4, wherein the container holder further comprises a guiding portion projecting radially outwards from the cylindrical portion and wherein the guiding portion is at least partially tapered in the distal direction.

9. An assembly according to claim 8, further comprising guide rails for guiding the guiding portion of the container holder, wherein the guiding portion of the container holder is received within the guide rails of the housing.

10. The assembly according to claim 4, wherein when the container holder is fit within the housing, the one or more internal projections of the housing project between the plurality of flexible arms of the container holder.

11. The assembly according to claim 10, wherein the housing at least partially encloses the plurality of flexible arms to prevent the plurality of flexible arms from flexing radially outwards.

12. The assembly according to claim 4, wherein the housing further comprises one or more windows provided proximally from the one or more internal projections and offset along the circumferential direction from the one or more internal projections, wherein the number of the one or more windows in the housing is equal to the number of the plurality of flexible arms and wherein the plurality of flexible arms block the one or more widows.

* * * * *